(12) United States Patent
Shapiro

(10) Patent No.: US 6,423,326 B1
(45) Date of Patent: Jul. 23, 2002

(54) COLD-MIX WATER-IN-OIL EMULSIONS COMPRISING QUATERNARY AMMONIUM COMPOUNDS AND PROCESS FOR PRODUCING SAME

(75) Inventor: Irene Shapiro, Buffalo Grove, IL (US)

(73) Assignee: Stepan Company, Northfield, IL (US)

( * ) Notice: Subject to any disclaimer, the term of this patent is extended or adjusted under 35 U.S.C. 154(b) by 0 days.

(21) Appl. No.: 09/627,783

(22) Filed: Jul. 27, 2000

Related U.S. Application Data

(60) Provisional application No. 60/146,597, filed on Jul. 30, 1999.

(51) Int. Cl.$^7$ .............................. A61K 7/00; A61K 9/42; B01F 17/00; B01F 3/08; C09K 3/00
(52) U.S. Cl. ..................... 424/401; 424/59; 424/400; 514/847; 514/873; 514/937; 516/21; 516/28
(58) Field of Search .................... 424/400, 401, 424/59; 514/847, 873, 937; 516/21, 28

(56) References Cited

U.S. PATENT DOCUMENTS

| | | |
|---|---|---|
| 4,389,418 A | 6/1983 | Burton |
| 4,421,740 A | 12/1983 | Burton |
| 4,777,039 A | 10/1988 | Lang et al. |
| 5,213,792 A | 5/1993 | Grundmann et al. |
| 5,543,136 A | 8/1996 | Aldous |
| 5,589,177 A | 12/1996 | Herb et al. |
| 5,656,280 A | 8/1997 | Herb et al. |
| 5,756,108 A | 5/1998 | Ribier et al. |
| 5,759,557 A | 6/1998 | Epstein et al. |
| 5,759,558 A | 6/1998 | Epstein et al. |

FOREIGN PATENT DOCUMENTS

| | | |
|---|---|---|
| EP | 654259 | 5/1995 |
| EP | 715842 A2 | 6/1996 |
| WO | WO98/55086 | 12/1998 |

*Primary Examiner*—Jose G. Dees
*Assistant Examiner*—Marina Lamm
(74) *Attorney, Agent, or Firm*—McDonnell Boehnen Hulbert & Berghoff

(57) ABSTRACT

The present invention relates to stable cold-mix water-in-oil emulsions and methods for preparing such emulsions. The cold-mix water-in-oil emulsions comprise oil (i.e., an emollient), water and an emulsification system comprising a quaternary ammonium-based low HLB emulsifier and optional co-emulsifiers. The emulsions are useful in preparing finished cosmetic compositions in the form of lotions, gels, or sprays, which provide improved moisturization, skin feel, skin care, and/or appearance benefits and/or reduced greasiness, with excellent rub-in and absorption characteristics. Also disclosed are cold-mix water-in-oil sunscreen emulsions and methods for preparing such sunscreen emulsions. The emulsions of the instant invention are generally capable of being substantially completely emulsified and stable at about 25° C.

28 Claims, No Drawings

COLD-MIX WATER-IN-OIL EMULSIONS COMPRISING QUATERNARY AMMONIUM COMPOUNDS AND PROCESS FOR PRODUCING SAME

This application claims the benefit of U.S. Provisional Application No. 60/146,597, filed Jul. 30, 1999.

BACKGROUND OF THE INVENTION

Field of the Invention

The present invention relates to stable cold-mix water-in-oil emulsions and methods for preparing such emulsions. More specifically, the invention relates to cold-mix water-in-oil emulsions comprising oil (i.e., an emollient), water and an emulsification system comprising a quaternary ammonium-based low HLB emulsifier and optional co-emulsifiers. The present invention relates to cosmetic compositions which contain the inventive cold-mix oil and water emulsions. These cosmetic compositions are typically in the form of lotions, gels, or sprays, which provide improved moisturization, skin feel, skin care, and appearance benefits and reduced greasiness, together with excellent rub-in and absorption characteristics. The instant invention also relates to cold-mix water-in-oil sunscreen emulsions and methods for preparing such sunscreen emulsions. The emulsions of the instant invention generally display excellent extended duration stability characteristics at both normal and elevated temperatures.

DESCRIPTION OF RELATED ART

Conventional cosmetic cream and lotion compositions, for example those in Sagarin, *Cosmetics Science and Technology*, 2nd Ed., Vol.1, Wiley Interscience (1972) and *Encyclopedia of Chemical Technology*, 3rd Ed., Vol. 7 are known to provide varying degrees of emolliency, barrier and water-retention (moisturizing) benefits. However, these conventional compositions are often lacking in desirable skin feel properties (i.e., they often feel very greasy when applied to the skin), as well as having poor rub-in, absorption and residue characteristics. Additional oil-in-water emulsion disclosures include for example those found in U.S. Pat. No. 5,759,558 (to Epstein, issued Jun. 2, 1998), U.S. Pat. No. 5,656,280 (to Helene Curtis, issued Aug. 12, 1997), U.S. Pat. No. 5,589,117 (to Helene Curtis, issued Dec. 31, 1996), U.S. Pat. No. 5,756,108 (to L'Oreal, issued May 26, 1998), U.S. Pat. No. 5,759,557 (to Epstein, issued Jun. 2, 1998), U.S. Pat. No. 5,543,136 (to NuSkin International, issued Aug. 6, 1996), U.S. Pat. No. 4,389,418 (to S. C. Johnson & Sons, issued Jun. 21, 1983), EP 0715842 A2 (Helene Curtis, filed Nov. 10, 1995), and WO 98/55086 (Stewart, filed Jun. 4, 1998).

While water-in-oil compositions are well known, they are difficult to prepare as they normally require heating to high temperatures (i.e., greater than 50° C.) and generally have not enjoyed commercial success and/or consumer popularity due to unacceptable greasiness. The disadvantages of preparing water-in-oil emulsions at higher temperatures include promotion of unacceptable water loss through evaporation, time-consummation, inefficient processing, and the added processing expense of heating the emulsion.

The foregoing description of the related art indicates that a variety of water-in-oil emulsions are known, along with a variety of processes to produce such emulsions, all of which have various end-use property limitations and/or undesirable processing limitations. A need exists for a superior processable water-in-oil emulsion which can be prepared at relatively low temperatures, i.e., at about 25° C. Additionally there is a need for such processable emulsions which do not impart a greasy feel to skin upon application, while at the same time such emulsion possess acceptable rub-in, absorption and residue characteristics.

Surprisingly, compositions of the instant invention can be prepared with little to no heat, i.e., they are prepared as a water-in-oil emulsion which is capable of being substantially completely emulsified and stable at about 25° C. In additional to highly desirable low temperature preparation, these emulsions are stable, light and have a non-greasy feel when applied to the skin. The present invention provides skin-care cosmetic compositions which provide improved moisturization, absorption, skin feel, skin care and appearance characteristics and, which in particular, provide improved short and longer term moisturizing effectiveness, while at the same time reducing stickiness and avoiding a greasy feel on the skin. The compositions also display excellent stability characteristics at both normal and elevated temperatures.

It is therefore an object of the present invention to provide cold-mix water-in-oil emulsions comprising oil (i.e., an emollient), water and an emulsification system comprising a quaternary ammonium-based low HLB emulsifier and optional co-emulsifiers. Another object of the invention is to provide cold-mix water-in-oil sunscreen emulsions comprising oil (i.e., an emollient), water, an emulsification system comprising a quaternary ammonium-based low HLB emulsifier and optional co-emulsifiers, and a sun screen agent. Another objection of the invention relates to bulk and finished cosmetic compositions (lotions, gels, sprays) which contain the inventive cold-mix water-in-oil emulsions and cold-mix water-in-oil sunscreen emulsions. The invention further relates to cold-mix methods of preparing the cold-mix water-in-oil emulsions disclosed, including the cold-mix water-in-oil sunscreen emulsions described herein.

It is another object of the present invention to provide methods for moisturizing and/or providing sun protection to human skin, comprising applying to the skin the cold-mix water-in-oil emulsions and/or the cold-mix water-in-oil sunscreen emulsions described herein.

These and other objects and advantages are achieved by the invention description below.

SUMMARY OF THE INVENTION

It has been surprisingly discovered that highly stable water-in-oil emulsions can be prepared as a cold mix water-in-oil emulsions at about 25° C. The present invention also encompasses cold mix water-in-oil sunscreen emulsions.

Accordingly, the present invention encompasses a cold-mix water-in-oil emulsion comprising:

(a) from about 10% to about 50% by weight of an emollient;

(b) from about 0.5% to about 30% by weight of an emulsification system comprising a low HLB emulsifier of the formula:

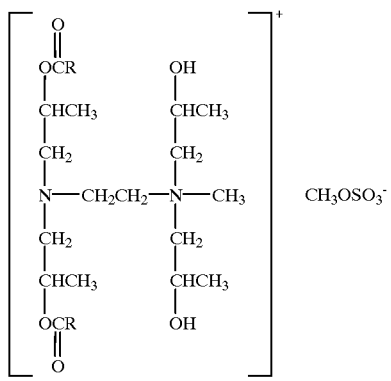

where R is substantially linear nor-oleyl;
(c) from about 0% to about 35% of a co-emulsifier; and
(d) water;
the emulsification system and co-emulsifier substantially permanently maintaining the water and emollient as an emulsion, the emulsion capable of being substantially completely emulsified and stable at about 25° C.

The present invention encompasses a cold-mix water-in-oil sunscreen emulsion comprising:
(a) from about 10% to about 30% by weight of an emollient; and
(b) from about 0.5% to about 30% by weight of an emulsification system comprising a low HLB emulsifier of the formula:

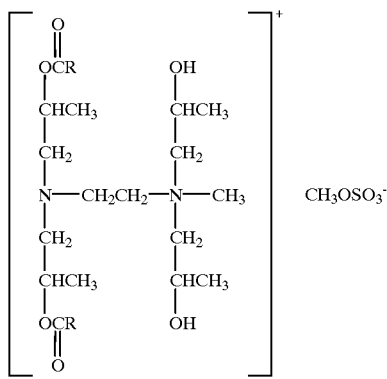

where R is substantially linear nor-oleyl;
(c) from about 0% to about 35% a co-emulsifier;
(d) a sunscreen agent; and
(e) water;
wherein the emulsification system and the co-emulsifier substantially permanently maintain the water and emollient as a sunscreen emulsion, the sunscreen emulsion capable of being substantially completely emulsified and stable at about 25° C.

The invention also includes methods for making and using such emulsions. The emulsions described herein are primarily useful in finished sun screening formulations for application to human skin and in finished moisturizing creams, lotions, gels, and sprays for application to human skin. The inventive emulsions may be topically applied to human skin to moisturize the skin and/or may also be applied to human skin before prolonged exposure to light radiation to prevent the erythema normally observed after such exposure, i.e. the prevention of sun burn.

DETAILED DESCRIPTION OF THE INVENTION

The present invention encompasses novel cold-mix water-in-oil emulsions utilizing quaternary ammonium-based low HLB emulsifiers. The emulsions are readily prepared at low temperatures, i.e. at about 25° C. Further, the emulsification system and the co-emulsifier substantially permanently maintain the water and emollient as a water-in-oil emulsion, where such emulsion is substantially completely emulsified and stable at about 25° C.; by this it is meant that the water-in-oil emulsion and/or water-in-oil sunscreen emulsion remains substantially completely emulsified and does not phase separate in two or more layers (e.g., a water layer and an oil layer) at 25° C. for a minimum of 14 days.

The emulsions of the instant invention preferably contain sufficient amounts of ingredients that will produce an emulsion having a smooth, continuous appearance when emulsified. The term "low HLB emulsifier" as used herein means an emulsifier with an HLB below 12, and preferred HLB below 10. The term "HLB" as used herein means Hydrophilic-Lipophilic Balance. HLB is a reflection of the balance between the lipophilic and hydrophilic moieties of a molecule (surfactant or emulsifier), such as the low HLB emulsifiers described herein. This balance between the lipophilic and hydrophilic moieties of a molecule provides an HLB number that indicates the surfactant's or emulsifiers performance as an emulsifier. A lower HLB value indicates a more lipophilic surfactant, which is accordingly more oil-soluble. HLB values may be calculated by a variety of know methods to those skilled in the art. (See for example: Rosen, Surfactants and Interfacial Phenomena, $2^{nd}$ ed., Wiley Interscience, 1989.)

As previously mentioned, the present invention encompasses a cold-mix water-in-oil emulsion comprising:
(a) from about 10% to about 50% by weight of an emollient;
(b) from about 0.5% to about 30% by weight of an emulsification system comprising a low HLB emulsifier of the formula:

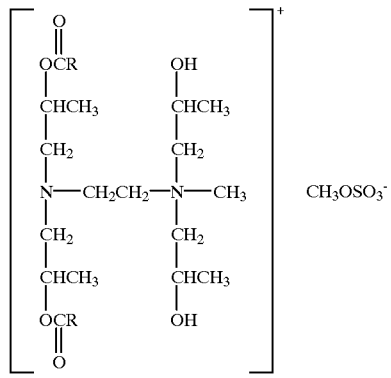

where R is substantially linear nor-oleyl;
(c) from about 0% to about 35% of a co-emulsifier; and
(d) water;
the emulsification system and co-emulsifier substantially permanently maintaining the water and emollient as an emulsion, the emulsion capable of being substantially completely emulsified and stable at about 25° C. More preferably the cold-mix water-in-oil emulsion comprises from about 10% to about 30% by weight of the emollient, and most preferably from about 15% to about 25% by weight of the emollient. In a somewhat preferred embodiment, the cold-mix water-in-oil emulsion will comprise from about 0.5% to about 15% by weight of the low HLB emulsifier, more preferably from about 0.5% to about 8% by weight of the low HLB emulsifier, and most preferably from about 1% to about 3% by weight of the low HLB emulsifier.

Useful emollients are described in detail below. Preferred emollients are dimethicone, cyclomethicone, triglycerides, alcohol esters, ethoxylated esters, hydrocarbons, natural oils or a mixture thereof. Of these preferred emollients, the preferred hydrocarbon are mineral oil, mineral spirits, isohexadecane, or a mixture thereof. The most preferred emollients are triglycerides, alcohol esters, ethoxylated esters, glycol ethers, natural oils or a mixture thereof. Of these, preferred natural oils include safflower oil, jojoba oil, sunflower oil, or a mixture thereof.

The cold-mix water-in-oil emulsion of the invention can additionally comprise a water-soluble nonionic surfactant. Preferred water-soluble nonionic surfactants are selected from the group consisting of polyethylene glycol laurate, polyethylene glycol dilaurate, or a mixture thereof.

In another preferred embodiment, the cold-mix water-in-oil emulsion comprises from about 0.2% to about 22.5% by weight of the co-emulsifier, more preferably from about 0.2% to about 12.0% by weight of the co-emulsifier and most preferably from about 0.4% to about 4.5% by weight of the co-emulsifier.

A preferred co-emulsifier is a dimethicone copolyol, selected from the group consisting of a cyclomethicone-dimethicone copolyol mixture, lauryl dimethicone copolyol, cetyl dimethicone copolyol, cetyl dimethicone copolyol/polyglyceryl-4-isostearate/hexyl laurate, or a mixture thereof, and highly preferred a mixture of cetyl dimethicone copolyol and lauryl dimethicone copolyol. The ratio of the low HLB emulsifier to the copolyol is preferably from about 1:1.5 to about 2.5:1.

The cold-mix water-in-oil emulsion may further comprising from 0% to about 10% by weight an alpha-hydroxy acid, a beta-hydroxy acid, or a mixture thereof, a lightening agent, or a tanning agent (e.g. dihydroxy acetone).

The present invention encompasses a cold-mix method for preparing a cold mix water-in-oil emulsion comprising:
(a) preparing an oil phase by combining an emollient and a co-emulsifier at about 25° C.;
(b) preparing an aqueous phase by combining a low HLB emulsifier of the formula:

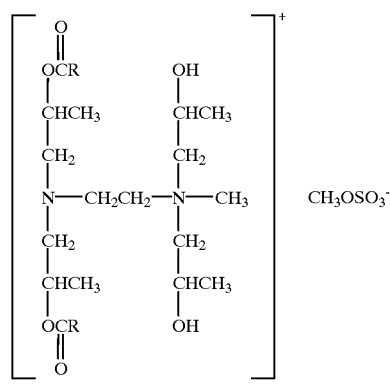

where R is substantially linear nor-oleyl, with water;
(c) combining the aqueous phase and the oil phase with agitation to produce an intermediate mixture;
(d) emulsifying the intermediate mixture to produce a water and oil emulsion which is substantially completely emulsified and stable at about 25° C.

The method for preparing a cold mix water-in-oil emulsion may further comprise homogenizing the water-in-oil emulsion. The method for preparing a cold mix water-in-oil emulsion may further comprise adding to the water-in-oil emulsion an alpha-hydroxy acid, a beta-hydroxy acid, or a mixture thereof, a lightening agent, or a tanning agent (e.g. dihydroxy acetone). The preferred method embodiments, more preferred embodiments and most preferred embodiments include those preferred components, ingredients, and ratios described herein.

The present invention encompasses a cold-mix water-in-oil sunscreen emulsion comprising:
(a) from about 10% to about 30% by weight of an emollient; and
(b) from about 0.5% to about 30% by weight of an emulsification system comprising a low HLB emulsifier of the formula:

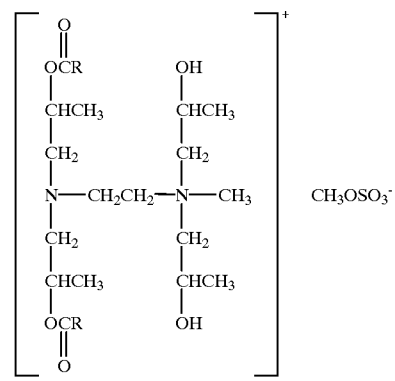

where R is substantially linear nor-oleyl;
(c) from about 0% to about 35% a co-emulsifier;
(d) from about 0.1% to about 15% by weight of a sunscreen agent; and
(e) water;
wherein the emulsification system and the co-emulsifier substantially permanently maintain the water and emollient as a sunscreen emulsion, the sunscreen emulsion capable of being substantially completely emulsified and stable at about 25° C.

The preferred cold-mix water-in-oil sunscreen emulsion embodiments, more preferred embodiments and most preferred embodiments include those preferred components, ingredients, and ratios described herein. Preferred sunscreens are titanium dioxide, zinc oxide, octyl methoxycinnamate, octyl salicylate avobenzone, benzophenone-4, or a mixture thereof.

The cold-mix water-in-oil sunscreen emulsion may also further comprising an alpha-hydroxy acid, a beta-hydroxy acid, or a mixture thereof, a lightening agent, or a tanning agent (e.g. dihydroxy acetone).

The present invention encompasses a cold-mix method for preparing a cold mix water-in-oil sunscreen emulsion comprising:
(a) preparing an oil phase by combining an emollient and a co-emulsifier at about 25° C.;
(b) preparing an aqueous phase by combining a low HLB emulsifier of the formula:

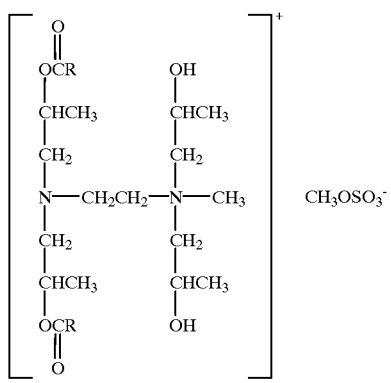

where R is substantially linear nor-oleyl, with water;
  (c) combining the aqueous phase and the oil phase with agitation to produce an intermediate mixture;
  (d) emulsifying the intermediate mixture to produce a water-in-oil emulsion which is substantially completely emulsified and stable at about 25° C.; and
  (e) combining a sunscreen agent with the water-in-oil emulsion to produce a water-in-oil sunscreen emulsion which is substantially completely emulsified and stable at about 25° C.

The method for preparing a cold mix water-in-oil sunscreen emulsion may further comprise homogenizing the water-in-oil emulsion. The method for preparing a cold mix water-in-oil sunscreen emulsion may further comprise adding to the water-in-oil emulsion an alpha-hydroxy acid, a beta-hydroxy acid, or a mixture thereof, a lightening agent, or a tanning agent (e.g. dihydroxy acetone). The preferred method embodiments, more preferred embodiments and most preferred embodiments include those preferred components, ingredients, and ratios described herein.

The present invention further encompasses a method for providing sun protection to human skin, comprising applying to said human skin a cold-mix water-in-oil sunscreen emulsion comprising:
  (a) from about 10% to about 30% by weight of an emollient;
  (b) from about 0.5% to about 30% by weight of an emulsification system comprising a low HLB emulsifier of the formula:

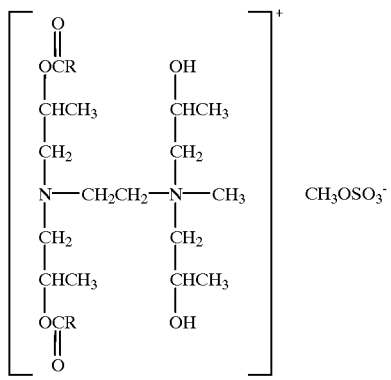

where R is substantially linear nor-oleyl;
  (c) from about 0% to about 35% a co-emulsifier;
  (d) from about 0.1% to about 15% by weight of a sunscreen agent; and
  (e) water;

wherein the emulsification system and the co-emulsifier substantially permanently maintain the water and emollient as a sunscreen emulsion, the sunscreen emulsion capable of being substantially completely emulsified and stable at about 25° C.

In another embodiment of the method for providing sun protection to human skin, the water-in-oil sunscreen emulsion additionally comprises an alpha-hydroxy acid, a beta-hydroxy acid, or a mixture thereof, a lightening agent, or a tanning agent (e.g. dihydroxy acetone) or a mixture thereof. The preferred methods for providing sun protection to human skin embodiments, more preferred embodiments and most preferred embodiments include those preferred components, ingredients, and ratios described herein.

Emollients

Water-in-oil compositions of the invention generally comprise from 5–65% by weight, more preferably from 10–40% by weight, most preferably 15–25% by weight of an emollient, i.e., the oil phase. The oil phase may generally comprise any oily material that is immiscible with water. Preferred oil phase emollients emulsion include those mentioned herein.

Optional Silicones

Silicone oils or fluids are used to improve the lubricity of the composition during application to the skin, as known to one of skill in the art. These silicone oils may optionally be included in the water-in-oil emulsions disclosed herein in minor amounts of about 0.5% to about 10% by weight. Preferably the viscosity of the optional silicone oil is from about 5 to about 12,500 centistokes at about 25° C. Examples of suitable optional silicone oils are dimethylpolysiloxane, diethylpolysiloxane, dimethylpolysiloxane-diphenylpolysiloxane, cyclomethicone, trimethylpolysiloxane, diphenylpolysiloxane, and mixtures thereof.

Alternatively the oil phase emollient may comprise further optional diluents such as, for example, low viscosity silicones (having a viscosity of between 0.1 to 1,000 mPa.s, more preferably 0.5 to 500 mPa.s, most preferably 0.65–100, liquid paraffins or methicones and other solvents such as $C_{10}$ to $C_{12}$ isoparaffins, including for example Isopar L (manufactured Esso), polyisobutene such as polysynlane (manufactured by Nippon Oils and Fats), squalane such as Squalene (manufactured by J. G. Marthens), branched chain hydrocarbons e.g., Permethyl 99A (manufactured by Presperse), Permethyl 101A, branched chain light paraffin oils such as Lytol (manufactured by Witco) or WM1 (manufactured by BP), mineral oil such as Marchol 82 (manufactured by Esso) or Carnation Oil (manufactured by Witco), long chain alkyl alkanoic esters such as decyl oleate (e.g., Cetiol V manufactured by Henkel), isopropyl myristate (e.g., Estol 1514 manufactured by Unichema) and glyceryl tri(2-ethyl hexanoate) e.g., Myritol CTEG manufactured by Henkel).

In somewhat more preferred embodiments, the optional silicone oil will comprise a cyclomethicone or dimethicone. Generally such optional silicones may be represented by the formula:

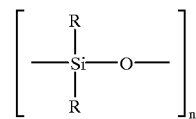

wherein R is a 1 to 3 carbon alkyl group, n is a number from 3 to 10, preferably from 3 to 7, and the unsatisfied valences on the oxygen and silicon atoms at the ends of the chain may optionally be joined to one another to form a cyclic structure. Suitable optional volatile silicones are, for example, U.C.C. Y-7207, sold by Union Carbide Corporation in which each R (based on the above structure) is methyl and which typically comprises by weight 99.4% tetramer, 0.6% trimer and traces of the pentamer and hexamer; SWS-03314, sold by SWS Silicones, a Division of Stauffer Chemical Company, in which R based on the above structure) is methyl and which is substantially all pentamer; and Dow Corning 345 fluid, sold by Dow Corning, Inc., in which R (based on the above structure) is methyl and which typically comprises by weight about 88% pentamer, about 11.8% tetramer and traces of trimer and hexamer.

Dimethicone, a dimethylpolysiloxane end blocked with trimethyl units, having a viscosity between 10 and 1000 centistokes is a particularly preferred optional silicone agent. In addition, other optional volatile silicones may also be utilized, alone or in combination with optional non-volatile silicones.

It is also possible to employ optional vegetable oils, animal oils, (For oil-in-water emulsions, compositions may also be prepared to contain various petroleum products and lubricants, graphite lubricants, polybutene, polyethylene, linseed oil, and crude oil, as well as other oils and other solid or semi-solid materials.

The oils that may be used in the emulsions also include solvents and hydrocarbons such as, for example, mineral spirits, kerosene, terpenes, and glycol ethers. The oils may also be materials suitable for personal care products, e.g., mineral oil, caprylic/capric triglyceride, isopropyl myristate, isopropyl palmitate, octyl palmitate, octyl isonononoate alkyl, esters of fatty acids having at least about 8 carbon atoms, or liquid alkyl esters of long chain fatty acids.

A particularly preferred copolyol of the instant invention is cetyl dimethicone copolyol, available from T. H. Goldschmidt as Abil® EM-90. The most preferred ratio of the low HLB emulsifier to copolyol is from about 1:1 to about 2:1. It is preferred that the low HLB emulsifier of the invention be used in combination with a co-emulsifier although the co-emulsifier is not a required component.

The Aqueous Phase

Water-in-oil compositions of the invention comprise from 35–95% by weight, more preferably from 60–90% by weight, most preferably from 75–85% by weight of an aqueous phase. The aqueous phase typically contains the low HLB emulsifier and water. In addition, the aqueous phase may for example further comprise one or more optional liquid water-miscible materials. Suitable optional materials are for example propylene glycol, glycerol, sorbitol and polyglycerol. Also suitable are polyether materials such as for example polyethyleneglycol or polypropylene glycol, ethoxylated polyols, e.g. Atlas G2330 manufactured by ICI and Glucum E10 manufactured by Amerchol and block copolymers of ethylene oxide and propylene oxide e.g. Synperonic L13 or ICI.

The aqueous phase comprises 0–75% by weight of the optionally liquid water-miscible materials, more preferably 20–65%, most preferably 30–45%, based on the weight of the aqueous phase.

Salts

Salts are sometimes optionally used to adjust the viscosity of cationic emulsions. However, in a distinct aspect of this invention, it has been found that salt in higher concentrations tends to destabilize the formulations of the present invention. It is preferred that the formulation be prepared in the substantial absence of added salt. The term "added salt" is meant to exclude salts formed as a consequence of adjusting the pH of other components added to the formulation. In more preferred embodiments of this invention, the total salt concentration of the formulation will be no more than 0.5 molar and more preferably is within the range from about 0.1 to about 0.2 molar.

The optional electrolyte material may be selected from water soluble salts such as alkali (earth) metal salts such as sulphates, halogenides, formates, borates, benzoates, and ($C_{1-4}$)tetra-alkyl ammonium halides etc. Water soluble acids such as citric acid, and phosphoric acid may also optionally be used in minor amounts as prescribed above. Water soluble bases such as sodium hydroxide may also optionally be used.

Physical Form

Water-in-oil emulsions according to the invention may take a variety of physical forms, for example they may be sprayable liquids, liquids, gels, pastes, etc. Preferably emulsions of the invention are flowable having a viscosity of about 2000–4500 cps, with lotion preferred viscosities of about 3000 to 4000 at 25° C., measured in a Brookfield RVT viscometer, spindle #4, 20 rpm. In another embodiment, emulsions of the instant invention may also be readily flowable, water-thin, "spray on lotions" with much lower viscosities of about 10–50 cps.

Other Ingredients

Water-in-oil emulsions of the invention may also include minor amounts of other optional ingredients such as surfactants, antibacterial agents, antidandruff agents, pearlescers, dyes, preservatives, sunscreens, viscosity modifiers, proteins, polymers, buffering agents, herb extracts, oils etc. Generally, these materials are only present in minor amounts, i.e., less that 3% by weight.

Sunscreens

Other ingredients can be employed in the inventive emulsions to provide a specifically tailored cosmetic composition. Sunscreens are cosmetic compositions which are applied topically to human skin to provide protection against the harmful ultraviolet rays of the sun (UV-A and UV-B radiation, generally in the range of 290–400 nm). Conventional sunscreens are prepared using cosmetically acceptable lotions, oils, creams, and emulsions (both oil-in-water and water-in-oil). For example, a sun screen additive, such as octyl dimethyl para-aminobenzoic acid can be employed in the inventive composition in amounts preferably from about 1% to 8% by weight of the total composition. To provide a skin protectant composition, zinc oxide, titanium dioxide, and like ingredients can also be provided in amounts from about 0.1% to 15.0%, preferably from 1.0% to 10.0% by weight of the composition.

Preferred organic sunscreen agents include benzophenone-3 (oxybenzone), benzophenone-4, menthyl anthranilate, octocrylene, octyl methoxycinnamate, and mixtures thereof. Other sunscreen agents such as octyl salicylate, PABA and derivatives may be used. When the emulsion contains octyl methoxycinnamate ("OMC"), an amount up to 10.0%, by weight of the total emulsion may be used.

Other ultraviolet protection agents that may be included in the emulsions include para-aminobenzoic acid, amido carboxylates (functionalized metallo soaps) such as lauryl succinamate, and aluminum stearate (lactate) (see e.g., U.S. Pat. Nos. 4,675,422 and 4,724,174).

Fatty Alcohols

Without being bound by any particular theory, fatty alcohols (typically monohydric alcohols) used in the formulations of the invention stabilize the emulsions and provide a cosmetically acceptable viscosity. Selection of the fatty alcohol is not critical although C10, C12, C14 fatty alcohols are preferred, with C12 being the most preferred. When used, the fatty alcohol is preferably included in the formulations of this invention at a concentration of about 0.3% to about 10% by weight of the emulsion composition, more preferably from about 0.5% to about 5% by weight.

Fatty Esters

Fatty ester emollients enhance the tactile properties of the composition. Examples of suitable fatty esters for use in the formulation of the invention include isopropyl myristate, isopropyl palmitate, isopropyl isostearate, isostearyl isostearate, diisopropyl sebacate, propylene glycol dipelargonate, 2-ethylhexyl isononoate, 2-ethylhexyl stearate, C12–C16 fatty alcohol lactate, isopropyl lanolate, 2-ethyl-hexyl salicylate, and mixtures thereof. The presently preferred fatty ester is isopropyl palmitate, octyl isonononoate. The fatty ester when included is preferably included in the formulations of this invention at a concentration of about 0.25% to about 40% by weight of the emulsion composition, more preferably from about 1% to about 25% by weight.

Humectants

If desired, a humectant may be optionally present in the compositions of the invention. Without being bound by any particular theory, it has been postulated that humectants can be entrapped in the interstices of the surface stratum corneum, where they act as a hygroscopic agent, thus increasing the amount of water held in this area. The water is given up by the humectant, as required, to contribute to the softening of the skin surface. Such humectants can be employed in addition to or substituted partially for, the water component of the inventive emulsions.

The humectants employed in the formulations of this invention are water-soluble and are substantially nonionizable. By "substantially nonionizable" it is meant that no significant or detectable disassociation in water occurs. Suitable humectants for the formulations of this invention include glycerin, propylene glycol, sorbitol, polyethylene glycol, 1,2,6-hexanetriol, hydrogenated starch hydrolysate, inositol, mannitol, PEG-5 pentaerythritol ether, polyglyceryl sorbitol, xylitol, sucrose, and the like. A particularly preferred humectant is glycerin which, apart from its water binding properties, is postulated to also visually improve the surface of dry skin. The humectant when present is preferably included in the formulations of this invention at a concentration of about 0.2% to about 5% by weight of the emulsion composition.

Acidic Materials and Alpha-/Beta Hydroxy Acids

The use of weakly acidic components is optional in the present invention and is not believed critical, although alpha hydroxy acids are presently preferred if such components are employed in the emulsions. Preferred alpha-hydroxy acids are selected from the group consisting of citric acid, glycolic acid, glucuronic acid, galacturonic acid, alpha hydroxybutyric acid, alpha hydroxyisobutyric acid, lactic acid, malic acid, mandelic acid, mucic acid, pyruvic acid, alpha phenylactic acid, alpha phenylpyruvic acid, saccharic acid, tartaric acid, and tartronic acid. Glycolic acid, lactic acid, tartaric acid, and malic acid are particularly preferred.

Other preferred acids are hydroxy, dihydroxy, and keto analogs of amino acids. Examples include glyceric acid, beta phenyl lactic acid, beta phenyl pyruvic acid, alpha hydroxy isovaleric acid, alpha hydroxy isocaproic acid, 2,3-dihydroxybutanoic acid, and 2,6-dihydroxyhexanoic.

Other useful acids include hydroxymonocarboxylic acids, hydroxydicarboxylic acids, hydroxytricarboxylic acids, and keto acids. The hydroxy polycarboxylic acids may be provided as the alpha or beta analogs and may be present as free acids, peroxides, lactones, amides, esters, or salts. Illustrative of the variety of acids included are 2-hydroxyglutaric acid, 3,4-dihydroxyglutamic acid, 2,5-dihydroxy-6-aminohexanoic acid, acetopyruvic acid, acetyl pyruvic acid, beta-floropyruvic acid, tartaric acid, citric acid, 2-hydroxybenzoic acid (salicylic acid), 2-hydroxy-2-methylbutyric acid, 2-hydroxy isobutyric acid, mandelic acid, and 2-hydroxy caproic acid.

Other Optional Ingredients

Other ingredients which also may be optionally included are emulsifying agents, thickeners, moisturizers, preservatives, coloring agents, fragrances, antioxidants, lightening agents, tanning agents, and other active ingredients. As a medicament, various essential oils, such as menthol and the like, can be employed in minor amounts from 0.1% to 2% by weight of the composition.

The formulation may also contain other conventional additives employed in cosmetic emulsions. Such optional additives include aesthetic enhancers, natural extracts, fragrance oils, dyes, preservatives. Preferred aesthetic enhancers are polyquaternium 31 and aluminum starch octenylsuccinate.

Oil-in-Water Emulsions

In another embodiment of the instant invention, other applications for the low HLB emulsifier of this invention are oil-in-water emulsions. A skin care product is an oil-in-water emulsion for topical application which comprises from about 1% to about 8 weight %, most preferably from about 2% to 5% of a particular cationic emulsifier (i.e. a low HLB emulsifier), optionally, from about 0.2% to about 15 weight %, preferably from 1% to 7% of a water-soluble humectant, and, optionally, a pharmaceutically acceptable, weakly acidic material in an amount sufficient to adjust the pH of the finished emulsion to a value in the range of about 2.0 to about 4.5, preferably 3.0 to 4.0, when the emulsion is diluted with purified water to 10 times its weight. Optionally, these oil-in-water emulsions will include hydrogenated castor oil and/or microcrystalline wax.

METHOD OF PREPARATION

Water-in-oil emulsions of the invention may be prepared by any suitable method for the preparation of water-in-oil emulsions well know to those skilled in the art. A preferred method involves the separate preparation of the oil phase (i.e. the emollient) and the aqueous phase by mixing at about 25° C., followed by gradually adding the aqueous phase to the oil phase under stirring at about 25° C.

The input of mixing energy should be high and should be maintained for a time sufficient to form a water-in-oil emulsion having a smooth appearance (indicating the presence of relatively small micelles in the emulsion).

The water employed in the formulations and method of this invention is purified water obtained, e.g., by distilling ordinary tap water, by purifying ordinary water through an ion exchange resin, or by other techniques apparent to those skilled in the art.

Application

The skin care compositions of the present invention are topically applied in a conventional manner. In general, the compositions may be dispensed from a container and then gently applied to the skin. The compositions are rapidly absorbed and leave the skin with a soft and smooth appearance.

"Weight percent", as used throughout this specification and in the claims, refers to weight percent, based on total weight of the cold-mix emulsion, unless otherwise specified.

All documents, e.g., patents and journal articles, cited above or below are hereby incorporated by reference in their entirety. In the following examples, all amounts are stated in percent by weight of active material unless indicated otherwise. One skilled in the art will recognize that modifications may be made in the present invention without deviating from the spirit or scope of the invention. The invention is illustrated further by the following examples which are not to be construed as limiting the invention or scope of the specific procedures or compositions described herein. All levels and ranges, temperatures, results etc., used herein are approximations unless otherwise specified.

EXAMPLE 1

Cold-Mix Water-In-Oil Emulsion

Water-in-oil emulsions were prepared by first preparing a water phase comprising the low HLB emulsifier of the following formula, subsequently preparing the oil phase and combining the two phases with agitation at around 25° C., as further illustrated below.

| Ingredients | A % by wt. | B % | Functionality |
|---|---|---|---|
| PHASE A | | | |
| 1. D.I. Water | q.s. to 100.0 | q.s. to 100.0 | Diluent |
| 2. STEPANQUAT ® ML[1] | 2.0 | 2.0 | Conditioning agent, emulsifier |
| 3. KESSCO ® PEG 600 ML[2] | 0.5 | 0.5 | Emollient |
| PHASE B | | | |
| 4. Abil EM-90[3] | 1.0 | 1.0 | Co-emulsifier |
| 5. Silicone DC 345[4] | 20.0 | 20.0 | Emollient |
| 6. TiO$_2$ Kobo MT-100T[5] | 8.0 | 8.0 | Physical sunscreen agent |
| PHASE C | | | |
| 7. ZnO Z-COTE[6] | — | 2.0 | Physical/inorganic sunscreen agent |
| 8. NEOBEE ® M-5 COSMETIC[7] | — | 5.0 | Emollient, solvent |
| PHASE D | | | |
| 9. Preservative, color, fragrance Properties: | q.s. | q.s. | Additive |
| Appearance | Lotion | Lotion | |
| SPF | 25.0 | Not tested | |

[1]Quaternary Ammonium Compound (Stepan)
[2]Polyethylene Glycol 600 Monolaurate (Stepan)
[3]Cetyl dimethicone copolyol (Goldschmidt)
[4]Cyclomethicone (Dow Corning)
[5]Titanium Dioxide (Kobo).
[6]Zinc Oxide BASF.
[7]Caprylic/Capric Triglyceride (Stepan)

Mixing Procedure
1. Prepare phase A by combing items #1,2 and 3 at 25 C. with agitation.
2. Prepare phase B by combining items #4, 5 and 6 at 25 C. with agitation.
3. Combine phase A and phase B while maintaining good agitation at about 25° C. to form an intermediate batch.
4. Prepare phase C by combining items #7 and 8 (for Formulation B) at 25 C. with agitation. Add phase C to the intermediate batch at 25 C. with agitation. Mix well for 15–20 minutes to form a main batch
5. Add phase D to the main batch at 25 C. with agitation.
6. Homogenize the entire mixture for 3–5 minutes at 5000 rpm using Silverson mixer, Model #L4RT.

EXAMPLE 2

Cold-Mix Water-In-Oil Emulsion

| Ingredients | C % by wt. | D % | Functionality |
|---|---|---|---|
| PHASE A | | | |
| 1. D.I. Water | q.s. to 100.0 | q.s. to 100.0 | Diluent |
| 2. STEPANQUAT ® ML[1] | 2.0 | 2.0 | Conditioning agent, emulsifier |
| 3. KESSCO ® PEG 600 ML[2] | 0.5 | 0.5 | Emollient |
| PHASE B | | | |
| 4. KESSCO ® OCTYL ISONONANOATE[3] | 20.0 | — | Emollient |
| 5. Abil EM-90[4] | 1.0 | 1.0 | Co-emulsifier |
| 6. Silicone DC 345[5] | — | 20.0 | Emollient |
| PHASE C | | | |
| PHASE D | | | |
| 7. Preservative, color, fragrance Properties: | q.s. | q.s. | Additive |
| Appearance | Opaque lotion | | |

[1]Quaternary Ammonium Compound (Stepan)
[2]Polyethylene Glycol 600 Monolaurate (Stepan)
[3]Octyl Isonononoate (Stepan)
[4]Cetyl dimethicone copolyol (Goldschmidt).
[5]Cyclomethicone (Dow Corning).

Mixing Procedure
1. Prepare phase A by combining items #1,2 and 3 at 25 C. with agitation.
2. Prepare phase B by combining items #4, 5 and 6 at 25 C. with agitation.
3. Combine phase A and phase B while maintaining good agitation at about 25° C. to form an intermediate batch.
4. Add phase D to the intermediate batch at 25 C. with agitation.
5. Homogenize the entire mixture for 3–5 minutes at 5000 rpm using Silverson mixer, Model #L4RT.

EXAMPLE 3

Lotion With Exfoliating Agent (Water-In-Oil Emulsion)

| Ingredients | % by wt. | Functionality |
|---|---|---|
| PHASE A | | |
| 1. D.I. Water | q.s. to 100.0 | Diluent |
| 2. STEPANQUAT ® ML[1] | 2.0 | Conditioning agent, emulsifier |
| 3. KESSCO ® PEG 600 ML[2] | 0.5 | Emollient |
| PHASE B | | |
| 4. Abil EM-90[3] | 1.0 | Co-Emulsifier |
| 5. Silicone DC 345[4] | 20.0 | Emollient |

-continued

| Ingredients | % by wt. | Functionality |
|---|---|---|
| 6. Lipocol L[5] | 1.5 | Bodifying Agent |
| 7. GLYPURE (70% active) | 7.2 | Exfoliating Agent |
| PHASE C | | |
| PHASE D | | |
| 8. Preservative, color, fragrance | q.s. | Additive |
| Properties: | | |
| Appearance | Lotion-like | |
| pH | 3.0–3.5 | |
| SPF | | |

[1]Quaternary Ammonium Compound (Stepan)
[2]PEG 600 Monolaurate (Stepan)
[3]Goldschmidt (Cetyl dimethicone copolyol).
[4]Cyclomethicone (Dow Corning)
[5]Lauryl Alcohol (Lipo Chemicals Inc.)
[6]Glycolic Acid (DuPont Chemicals)

Mixing Procedure
1. Prepare phase A by combining items #1, 2 and 3 at 25 C. with agitation.
2. Prepare phase B by combining items #4, 5, 6 and 7 at 25 C. with agitation.
3. Combine phase A and phase B maintaining good agitation at about 25° C. to form an intermediate mixture.
4. Add phase D to the intermediate mixture at 25 C. with agitation.
5. Homogenize the entire mixture for 3–5 minutes at 5000 rpm using Silverson mixer, Model #L4RT.

EXAMPLE 4 Lotion With Inorganic Sunscreen (Water-In-Oil Emulsion)

| Ingredients | % by wt. | Functionality |
|---|---|---|
| PHASE A | | |
| 1. D.I. Water | q.s. to 100.0 | Diluent |
| 2. STEPANQUAT ® ML[1] | 2.0 | Conditioning agent, emulsifier |
| 3. KESSCO ® PEG 600 ML[2] | 0.5 | Emollient |
| PHASE B | | |
| 4. Abil EM-90[3] | 1.0 | Co-Emulsifier |
| 5. Silicone DC 345[4] | 20.0 | Emollient |
| PHASE C | | |
| 6. ZnO Z-COTE[5] | 5.0 | Physical/inorganic sunscreen agent |
| 7. NEOBEE ® M-5 COSMETIC[6] | 5.0 | Emollient, solvent |
| PHASE D | | |
| 8. Preservative, color, fragrance | q.s. | Additive |
| Properties: | | |
| Appearance | | |
| pH | | |
| SPF | | |

[1]Quaternary Ammonium Compound (Stepan)
[2]Polyethylene Glycol 600 Monolaurate (Stepan)
[3]Cetyl dimethicone copolyol (Goldschmidt).
[4]Cyclomethicone (Dow Corning)
[5]Zinc Oxide (BASF)
[6]Caprylic/Capric Triglyceride (Stepan).

Mixing Procedure
1. Prepare phase A by combining items #1, 2 and 3 at 25 C. with agitation.
2. Prepare phase B by combining items #4 and 5 at 25 C. with agitation.
3. Combine phase A and phase B while maintaining good agitation at about 25° C. to form an intermediate batch.
4. Prepare phase C by combining items #6 and 7 at 25 C. with agitation. Add phase C to the intermediate batch at 25 C. with agitation. Mix well for 15–20 minutes to form a main batch.
5. Add phase D to the main batch at 25 C. with agitation.
6. Homogenize the entire mixture for 3–5 minutes at 5000 rpm using Silverson mixer, Model #L4RT.

EXAMPLE 5 Sprayable Lotion With Organic Sunscreen (Water-In-Oil Emulsion)

| Ingredients | % by wt. | Functionality |
|---|---|---|
| PHASE A | | |
| 1. D.I. Water | q.s. to 100.0 | Diluent |
| 2. STEPANQUAT ® ML[1] | 2.5 | Conditioning agent, emulsifier |
| 3. KESSCO ® PEG 600 ML[2] | 0.5 | Emollient |
| PHASE B | | |
| 4. Abil EM-90[3] | 1.5 | Co-Emulsifier |
| 5. Silicone DC 345[4] | 10.0 | Emollient |
| 6. Parsol MCX[5] | 7.5 | Organic Sunscreen |
| 7. Escalol 587[6] | 5.0 | Organic Sunscreen |
| PHASE C | | |
| PHASE D | | |
| 8. Preservative, color, fragrance | q.s. | Additive |
| Properties: | | |
| Appearance | Sprayable, water-thin emulsion | |
| pH | | |
| SPF | | |

[1]Quaternary Ammonium Compound (Stepan)
[2]Polyethylene Glycol 600 Monolaurate (Stepan)
[3]Cetyl dimethicone copolyol (Goldschmidt).
[4]Cyclomethicone (Dow Corning)
[5]Octyl Methoxycinnamate (Roche Chemicals)
[6]Octyl Salicylate (ISP Van Dyk Inc.)

Mixing Procedure
1. Prepare phase A by combining items #1, 2 and 3 at 25 C. with agitation.
2. Prepare phase B by combining items #4, 5, 6 and 7 at 25 C. with agitation.
3. Combine phase A and phase B while maintaining good agitation at about 25 C. to form an intermediate batch.
4. Add phase D to the intermediate batch at 25 C. with agitation.
5. Homogenize the entire mixture for 3–5 minutes at 5000 rpm using Silverson mixer, Model #L4RT.

EXAMPLE 6 Not Sprayable Lotion With Organic Sunscreen (Water-In-Oil Emulsion)

| Ingredients | % by wt. | Functionality |
|---|---|---|
| PHASE A | | |
| 1. D.I. Water | q.s. to 100.0 | Diluent |
| 2. STEPANQUAT ® ML[1] | 2.5 | Conditioning agent, emulsifier |
| 3. KESSCO ® PEG 600 ML[2] | 0.5 | Emollient |
| PHASE B | | |
| 4. Abil EM-90[3] | 1.5 | Co-Emulsifier |
| 5. Permethyl 101A[4] | 10.0 | Emollient |

-continued

| Ingredients | % by wt. | Functionality |
|---|---|---|
| 6. Escalol 557[5] | 7.5 | Organic Sunscreen |
| 7. Escalol 587[6] | 5.0 | Organic Sunscreen |
| PHASE C | | |
| PHASE D | | |
| 8. Preservative, color, fragrance | q.s. | Additive |
| Properties: | | |
| Appearance | NOT Sprayable, thick emulsion | |
| pH | | |
| SPF | | |

[1]Quaternary Ammonium Compound (Stepan)
[2]Polyethylene Glycol 600 Monolaurate (Stepan)
[3]Cetyl dimethicone copolyol (Goldschmidt).
[4]Cyclomethicone (Dow Corning)
[5]Octyl Methoxycinnamate (ISP Van Dyk Inc.)
[6]Octyl Salicylate (ISP Van Dyk Inc.)

Mixing Procedure
1. Prepare phase A by combining items #1, 2 and 3 at 25 C. with agitation.
2. Prepare phase B by combining items #4, 5, 6 and 7 at 25 C. with agitation.
3. Combine phase A and phase B while maintaining good agitation at about 25 C. to form an intermediate batch.
4. Add phase D to the intermediate batch at 25 C. with agitation.
5. Homogenize the entire mixture for 3–5 minutes at 5000 rpm using Silverson mixer, Model #L4RT.

EXAMPLE 7

Cold Mixing Organic Sunscreen Emulsion (Water-In-Oil Emulsion)

| Ingredients | % by wt. | Functionality |
|---|---|---|
| PHASE A | | |
| 1. D.I. Water | q.s. to 100.0 | Diluent |
| 2. STEPANQUAT ® ML[1] | 2.5 | Conditioning agent, emulsifier |
| 3. KESSCO ® PEG 600 ML[2] | 0.5 | Emollient |
| PHASE B | | |
| 4. KESSCO ® Octyl Isononanoate[3] | 10.0 | Emollient |
| 5. Abil EM-90[4] | 1.5 | Co-Emulsifier |
| 6. Parsol MCX[5] | 7.5 | Organic Sunscreen |
| 7. Escalol 587[6] | 5.0 | Organic Sunscreen |
| 8. Lipocol L[7] | | |
| PHASE C | | |
| PHASE D | | |
| 9. Preservative, color, fragrance | q.s. | Additive |
| Properties: | | |
| Appearance | Cream | |
| pH | | |
| SPF | | |

[1]Quaternary Ammonium Compound (Stepan)
[2]Polyethylene Glycol 600 Monolaurate (Stepan)
[3]Octyl Isononanoate (Stepan)
[4]Goldschmidt (Cetyl dimethicone copolyol)
[5]Octyl methoxycinnamate (Roche Chemicals, Inc.)
[6]Octyl Salicylate (ISP Van Dyk, Inc.)
[7]Lauryl Alcohol (Lipo Chemicals, Inc.)

Mixing Procedure
1. Prepare phase A by combining items #1, 2 and 3 at 25 C. with agitation.
2. Prepare phase B by combining items #4, 5, 6 and 7 at 25 C. with agitation.
3. Combine phase A and phase B while maintaining good agitation at about 25C. to form an intermediate batch.
4. Add phase D to the intermediate batch at 25 C. with agitation.
5. Homogenize the entire mixture for 3–5 minutes at 5000 rpm using Silverson mixer, Model #L4RT.

EXAMPLE 8 Cold Mixing Organic Sunscreen Emulsion (Water-In-Oil Emulsion)

| Ingredients | % by wt. | Functionality |
|---|---|---|
| PHASE A | | |
| 1. D.I. Water | q.s. to 100.0 | Diluent |
| 2. STEPANQUAT ® ML[1] | 2.5 | Conditioning agent, emulsifier |
| 3. KESSCO ® PEG 600 ML[2] | 0.5 | Emollient |
| PHASE B | | |
| 4. KESSCO ® Octyl Palmitate[3] | 10.0 | Emollient |
| 5. Abil EM-90[4] | 1.5 | Co-Emulsifier |
| 6. Escalol 557[5] | 7.5 | Organic Sunscreen |
| 7. Escalol 587[6] | 5.0 | Organic Sunscreen |
| 8. Lipocol L[7] | | |
| PHASE C | | |
| PHASE D | | |
| 9. Preservative, color, fragrance | q.s. | Additive |
| Properties: | | |
| Appearance | Thin emulsion! | |
| pH | | |
| SPF | | |

[1]Quaternary Ammonium Compound (Stepan)
[2]Polyethylene Glycol 600 Monolaurate (Stepan)
[3]Octyl Palmitate (Stepan)
[4]Goldschmidt (Cetyl dimethicone copolyol)
[5]Octyl methoxycinnamate (ISP Van Dyk, Inc.)
[6]Octyl Salicylate (ISP Van Dyk, Inc.)
[7]Lauryl Alcohol (Lipo Chemicals, Inc.)

Mixing Procedure
1. Prepare phase A by combining items #1, 2 and 3 at 25 C. with agitation.
2. Prepare phase B by combining items #4, 5, 6 and 7 at 25 C. with agitation.
3. Combine phase A and phase B while maintaining good agitation at about 25C. to form an intermediate batch.
4. Add phase D to the intermediate batch at 25C. with agitation.
5. Homogenize the entire mixture for 3–5 minutes at 5000 rpm using Silverson mixer, Model #L4RT.

EXAMPLE 9 Comparative: Cold Mixing Organic Sunscreen Emulsion (Water-In-Oil Emulsion)

| Ingredients | % by wt. | Functionality |
|---|---|---|
| PHASE A | | |
| 1. D.I. Water | q.s. to 100.0 | Diluent |
| 2. AMMONYX ® CETAC[1] | 2.5 | Conditioning agent, emulsifier |
| 3. KESSCO ® PEG 600 ML[2] | 0.5 | Emollient |

-continued

| Ingredients | % by wt. | Functionality |
|---|---|---|
| PHASE B | | |
| 4. Silicone DC 345[3] | 10.0 | Emollient |
| 5. Abil EM-90[4] | 1.5 | Co-Emulsifier |
| 6. Escalol 557[5] | 7.5 | Organic Sunscreen |
| 7. Escalol 587[6] | 5.0 | Organic Sunscreen |
| 8. Lipocol L[7] | | |
| PHASE C | | |
| PHASE D | | |
| 9. Preservative, color, fragrance | q.s. | Additive |
| Properties: | | |
| Appearance | Thin emulsion | |
| pH | | |
| STABILITY | Separation in 1 hour | |

[1]Quaternary Ammonium Compound (Stepan)
[2]Polyethylene Glycol 600 Monolaurate (Stepan)
[3]Octyl Palmitate (Stepan)
[4]Goldschmidt (Cetyl dimethicone copolyol)
[5]Octyl methoxycinnamate (ISP Van Dyk, Inc.)
[6]Octyl Salicylate (ISP Van Dyk, Inc.)
[7]Lauryl Alcohol (Lipo Chemicals, Inc.)

Mixing Procedure

1. Prepare phase A by combining items #1, 2 and 3 at 25C. with agitation.
2. Prepare phase B by combining items #4, 5, 6 and 7 at 25C. with agitation.
3. Combine phase A and phase B while maintaining good agitation at about 25C. to form an intermediate batch.
4. Add phase D to the intermediate batch at 25C. with agitation.
5. Homogenize the entire mixture for 3–5 minutes at 5000 rpm using Silverson mixer, Model #L4RT.

EXAMPLE 10 Oil-In-Water Emulsion Transepidermal Water Loss Comparison

| Ingredients | A % by wt. | C (Comparative Example) % | Functionality |
|---|---|---|---|
| PHASE A | | | |
| 1. D.I. Water | q.s. to 100.0 | q.s. to 100.0 | Diluent |
| 2. STEPANQUAT ® ML[1] | 2.5 | — | Conditioning agent, emulsifier |
| 3. AMMONYX CETAC ®[2] | 2.5 | 2.5 | Conditioning agent, emulsifier |
| 4. Glycerin[3] | 4.0 | 4.0 | Humectant |
| PHASE B | | | |
| 5. Varisoft T-100[4] | — | 2.5 | Emulsifier/ Conditioning Agent |
| 6. KESSCO ® IPP[5] | 3.0 | 3.0 | Emollient |
| 1. White Fonoline (Petrolatum)[6] | 4.0 | 4.0 | Emollient |
| 2. DC Silicone 200[7] (350 cps) | 0.25 | 0.25 | Emollient |
| 9. KESSCO ® Cetyl Alcohol[8] | 2.0 | 2.0 | Bodifying Agent |

-continued

| Ingredients | A % by wt. | C (Comparative Example) % | Functionality |
|---|---|---|---|
| PHASE C | | | |
| PHASE D | | | |
| 10. Preservative, color, fragrance | q.s. | q.s. | Additive |
| Properties: | | | |
| Appearance | Lotion | Lotion | |

[1]Quaternary Ammonium Compound (Stepan)
[2]Cetrimonium Chloride (Stepan)
[3]Glycerol (J.T. Baker)
[4]Dimethyl Distearyl Ammonium Chloride (Sherex)
[5]Isopropyl Palmitate (Stepan)
[6]Petrolatum (Witco)
[7]Dimethicone (Dow Corning)
[8]Cetyl Alcohol (Stepan Co.)

Mixing Procedure

1. Prepare phase A by combining items #1, 2, 3 and 4 at 25C. with agitation.
2. Heat to phase A to 70–75 F.
3. Prepare phase B by adding items #5, 6, 7 and 8 at 25C. with agitation.
4. Heat phase B to 70–75 F.
5. Combine phase A and phase B while maintaining good agitation at 70–75 F. to form an intermediate batch.
6. Continue mixing the intermediate batch at 70–75 F. for 20–25 minutes.
7. Cool the intermediate batch to 30–35 F.
8. Add phase D to the intermediate batch at 30–35 F. with agitation to form a main batch.
9. Cool the main batch to about 25 C.
10. Homogenize the entire mixture for 3–5 minutes at 5000 rpm using Silverson mixer, Model #L4RT.

EXAMPLE 11 Cold Mixing Emulsion (Water-In-Oil Emulsion)

| Ingredients | % by wt. | Functionality |
|---|---|---|
| PHASE A | | |
| 1. D.I. Water | q.s. to 100.0 | Diluent |
| 2. STEPANQUAT ® ML[1] | 2.0 | Conditioning agent, emulsifier |
| 3. KESSCO ® PEG 600 ML[2] | 0.5 | Emollient |
| PHASE B | | |
| 4. KESSCO ® Octyl Isononanoate[3] | 20.0 | Emollient |
| PHASE C | | |
| PHASE D | | |
| 5. Preservative, color, fragrance | q.s. | Additive |
| Properties: | | |
| Appearance | Thin emulsion | |

[1]Quaternary Ammonium Compound (Stepan)
[2]Polyethylene Glycol 600 Monolaurate (Stepan)
[3]Octyl Isononanoate (Stepan)

Mixing Procedure
1. Prepare phase A by combining items #1, 2 and 3 at 25 C. with agitation.
2. Combine phase A and phase B while maintaining good agitation at about 25 C. to form an intermediate batch.
3. Add phase D to the intermediate batch at 25 C. with agitation.
4. Homogenizef the entire mixture for 3–5 minutes at 5000 rpm using Silverson mixer, Model #L4RT.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:
1. A cold-mix water-in-oil emulsion comprising:
    (a) from about 10% to about 50% by weight of an emollient;
    (b) from about 0.5% to about 30% by weight of an emulsification system comprising a low HLB emulsifier of the formula:

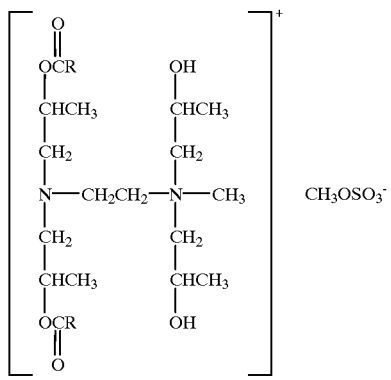

where R is substantially linear nor-oleyl;
    (c) from about 0% to about 35% of a co-emulsifier; and
    (d) water;
    the emulsification system and co-emulsifier substantially permanently maintaining the water and emollient as an emulsion, the emulsion capable of being substantially completely emulsified and stable at about 25° C.
2. A cold-mix water-in-oil emulsion according to claim 1, comprising from about 10% to about 30% by weight of the emollient.
3. A cold-mix water-in-oil emulsion according to claim 1, comprising from about 15% to about 25% by weight of the emollient.
4. A cold-mix water-in-oil emulsion according to claim 1, comprising from about 0.5% to about 15% by weight of the low HLB emulsifier.
5. A cold-mix water-in-oil emulsion according to claim 1, comprising from about 0.5% to about 8% by weight of the low HLB emulsifier.
6. A cold-mix water-in-oil emulsion according to claim 1, comprising from about 1% to about 3% by weight of the low HLB emulsifier.
7. A cold-mix water-in-oil emulsion according to claim 1, wherein the emollient is a dimethicone, a cyclomethicone, a triglyceride, an alcohol ester, an ethoxylated ester, a hydrocarbon, a natural oil or a mixture thereof.
8. A cold-mix water-in-oil emulsion according to claim 7, wherein the hydrocarbon is mineral oil, mineral spirits, isohexadecane, or a mixture thereof.
9. A cold-mix water-in-oil emulsion according to claim 1, wherein the emollient is a triglyceride, an alcohol ester, an ethoxylated ester, a glycol ether, a natural oil or a mixture thereof.
10. A cold-mix water-in-oil emulsion according to claim 9, wherein the natural oil is sunflower oil, jojoba oil, sunflower oil, or a mixture thereof.
11. A cold-mix water-in-oil emulsion according to claim 1, further comprising a water-soluble nonionic surfactant.
12. A cold-mix water-in-oil emulsion according to claim 11, wherein the water-soluble nonionic surfactant is selected from the group consisting of polyethylene glycol laurate, polyethylene glycol dilaurate, and a mixture thereof.
13. A cold-mix water-in-oil emulsion according to claim 1, comprising from about 0.2% to about 22.5% by weight of the co-emulsifier.
14. A cold-mix water-in-oil emulsion according to claim 1, comprising from about 0.2% to about 12.0% by weight of the co-emulsifier.
15. A cold-mix water-in-oil emulsion according to claim 1, comprising from about 0.4% to about 4.5% by weight of the co-emulsifier.
16. A cold-mix water-in-oil emulsion according to claim 1, wherein the co-emulsifier is a dimethicone copolyol.
17. A cold-mix water-in-oil emulsion according to claim 16, wherein the dimethicone copolyol is selected from the group consisting of a cyclomethicone-dimethicone copolyol mixture, lauryl dimethicone copolyol, cetyl dimethicone copolyol, cetyl dimethicone copolyol/polyglyceryl-4-isostearate/hexyl laurate, and a mixture thereof.
18. A cold-mix water-in-oil emulsion according to claim 1, wherein the emulsification system further comprises a copolyol which is a mixture of cetyl dimethicone copolyol and lauryl dimethicone copolyol.
19. A cold-mix water-in-oil emulsion according to claim 18, wherein the ratio of the low HLB emulsifier to the copolyol is from about 1:1.5 to about 2.5:1.
20. A cold-mix water-in-oil emulsion according to claim 1, further comprising an alpha-hydroxy acid, a beta-hydroxy acid, or a mixture thereof.
21. A cold-mix water-in-oil emulsion according to claim 1, further comprising a lightening agent.
22. A cold-mix water-in-oil emulsion according to claim 1, further comprising a tanning agent.
23. A cold-mix water-in-oil emulsion according to claim 22, wherein the tanning agent is dihydroxy acetone.
24. A cold-mix method for preparing a cold-mix water-in-oil emulsion comprising:
    (a) preparing an oil phase by combining an emollient and a co-emulsifier at about 25° C.;

(b) preparing an aqueous phase by combining a low HLB emulsifier of the formula:

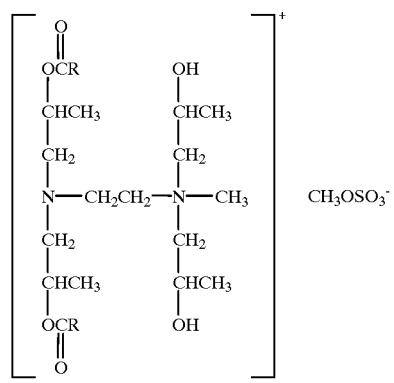 CH$_3$OSO$_3^-$ where R is substantially linear nor-oleyl, with water;

(c) combining the aqueous phase and the oil phase with agitation to produce an intermediate mixture;

(d) emulsifying the intermediate mixture to produce a water-in-oil emulsion which is substantially completely emulsified and stable at about 25° C.

25. A cold-mix method according to claim 24, further comprising homogenizing the water-in-oil emulsion.

26. A cold-mix method according to claim 24, wherein the emollient is a dimethicone, a cyclomethicone, a triglyceride, an alcohol ester, an ethoxylated ester, a hydrocarbon, a natural oil or a mixture thereof.

27. A cold-mix method according to claim 24, wherein the emollient is a triglyceride, an alcohol ester, an ethoxylated ester, a glycol ether, a natural oil or a mixture thereof.

28. A method for providing moisturization to human skin, comprising applying to said human skin a cold-mix water-in-oil emulsion comprising:

(a) from about 10% to about 30% by weight of an emollient;

(b) from about 0.5% to about 30% by weight of an emulsification system comprising a low HLB emulsifier of the formula:

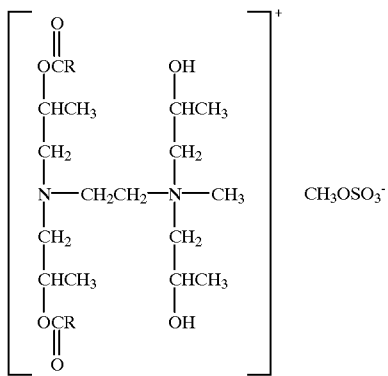 CH$_3$OSO$_3^-$ where R is substantially linear nor-oleyl;

(c) from about 0% to about 35% a co-emulsifier; and (d) water;

wherein the emulsification system and the co-emulsifier substantially permanently maintain the water and emollient as an emulsion, the emulsion capable of being substantially completely emulsified and stable at about 25° C.

* * * * *